United States Patent [19]

Hall et al.

[11] 4,213,831
[45] Jul. 22, 1980

[54] ALUMINUM CONTAINER FOR PROCESSING VINYLBENZYL CHLORIDES

[75] Inventors: Richard H. Hall, Midland; Daniel H. Haigh, Beaverton; Robert D. Hansen, Midland, all of Mich.

[73] Assignee: The Dow Chemical Company, Midland, Mich.

[21] Appl. No.: 302,231

[22] Filed: Oct. 30, 1972

[51] Int. Cl.$^2$ .............................................. B01D 3/00
[52] U.S. Cl. ........................... 203/86; 206/524.6; 220/83; 260/652 P; 526/62; 526/293
[58] Field of Search ............ 203/86, 6; 202/267; 260/652 R, 652 P; 206/84, 524.6; 220/83; 55/220; 526/62, 293

[56] References Cited

U.S. PATENT DOCUMENTS

| | | | |
|---|---|---|---|
| 2,072,053 | 2/1937 | Hendrey | 203/86 |
| 2,079,786 | 5/1937 | Beck | 206/86 |
| 2,543,971 | 3/1951 | Houpt et al. | 203/86 |
| 3,060,105 | 10/1962 | Muller | 203/86 |
| 3,274,077 | 9/1966 | Hoffenberg et al. | 260/651 R |
| 3,361,650 | 1/1968 | Egbert | 203/86 |
| 3,405,039 | 10/1968 | Raley, Jr. | 206/84 |

*Primary Examiner*—Wilbur L. Bascomb, Jr.
*Attorney, Agent, or Firm*—D. H. Thurston; G. R. Baker

[57] ABSTRACT

Unstabilized vinylbenzyl chloride and substituted vinylbenzyl chlorides are essentially inert with respect to surfaces of aluminum or alloys containing at least 90 percent by weight of aluminum in sharp contrast to benzyl chloride and similar substituted benzyl halides. Aluminum and such alloys of aluminum are thus practical materials of construction for making containers, pipes, stills, still column packing and the like for handling vinylbenzyl chloride.

4 Claims, No Drawings

ALUMINUM CONTAINER FOR PROCESSING VINYLBENZYL CHLORIDES

BACKGROUND OF THE INVENTION

The present invention concerns a new use of a material in an application where the material has heretofore been considered entirely inappropriate.

Aliphatically bound halogen is known to be relatively reactive with many metals, particularly active metals such as aluminum. The reactivity of certain halides such as carbon tetrachloride and methyl chloroform with aluminum and aluminum alloys is well known and has been responsible for a great deal of work in the field of solvent stabilization. Activated halides such as allyl chloride, benzyl chloride, and substituted benzyl halides are generally known to be particularly reactive, and such halides are customarily handled in special containers or apparatus constructed of resin-lined metal, glass, ceramic materials, nickel, titanium or tantalum. Such halides have been considered essentially equivalent in reactivity so that a particular material of construction has been assumed to be suitable or unsuitable for contact with all members of the class depending upon its behavior with respect to one or two members. For example, benzyl chloride is known to react vigorously with an aluminum surface and the presumption has been that substituted benzyl chlorides behave in the same way.

SUMMARY OF THE INVENTION

It has now been found, completely unexpectedly, that although benzyl chloride and most substituted benzyl chlorides do react so vigorously with aluminum and aluminum alloys that contact between these substances must be carefully avoided, vinylbenzyl chloride and substituted vinylbenzyl chlorides as defined below behave entirely differently in this respect. The defined vinylbenzyl chlorides have the formula

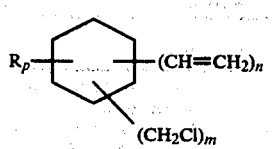

wherein R is an alkyl radical of 1-4 carbon atoms, m and n are independently one or two, and p is zero or one. These have been found to be so inert in the presence of a surface of aluminum or an alloy containing at least about 90 percent by weight of aluminum that such metals are suitable materials of construction for making shipping and storage containers, pipes, stills, or other processing equipment for containing, transferring, distilling, filtering, polymerizing, or otherwise processing these compounds without need for any stabilizer or inhibitor.

DETAILED DESCRIPTION

The peculiar unreactivity with aluminum is characteristic of all of the position isomers of the defined vinylbenzyl chlorides. Even the presence of water or small amounts of HCl, either anhydrous or aqueous, as in the crude material, has no significant effect. The presence or absence of atmospheric oxygen also appears to have no effect. The unreactivity persists at least to about 150° C. which covers those temperatures necessary in processing and is shown by both liquid and vapor phases. The only substantial deleterious changes observed in extended tests under these conditions are those caused by polymerization of the vinyl group.

It is thought that the reason for this unusual lack of reaction and corrosion of the metal surface is the formation of a protective film of some kind. Experiments wherein previous contact with a vinylbenzyl chloride appears to delay reaction when the metal surface is subsequently contacted with the reactive benzyl chloride seem to support this theory. Similarly, mixtures of benzyl chloride with substantial proportions of a vinylbenzyl chloride fail to react with aluminum.

The unreactivity of the defined vinylbenzyl chlorides with aluminum is particularly surprising in view of the fact that other closely related chlorides react vigorously, even at lower temperatures. Such reactive chlorides include benzyl chloride, ethylbenzyl chloride, and (1- and 2-chlorovinyl) toluene. Mixtures such as styrene plus benzyl chloride and vinyltoluene plus benzyl chloride are also reactive showing that a vinyl group per se is not an inhibitor to the reaction of benzyl chloride with aluminum.

The term aluminum is used herein, except where the distinction is made clear, to mean both essentially pure aluminum and alloys of at least 90% by weight aluminum content. Many such alloys are in commercial use and the alloying metals are typically one or more of the elements Si, Fe, Cu, Mn, Mg, Cr, Zn, and Ti. Less commonly used elements include Ni, Bi, Pb, Be, V, Zr, and B.

EXAMPLE 1

Liquid phase corrosion tests were run by refluxing vinylbenzyl chloride or other such chloride in contact with aluminum foil or coupon of sheet aluminum in a test tube with attached reflux condenser. These tests were made at 125° C. liquid temperature by maintaining the absolute pressure in the system at about 35 mm Hg. The aluminum used was either commercial aluminum foil or a coupon of sheet aluminum corresponding in analysis to aluminum 3003. VBC is used to designate mixed meta and para isomers of vinylbenzyl chloride in 60:40 ratio. The vinyltoluene, (α-chlorovinyl)toluene, and ethylbenzyl chloride tested were also mixed meta and para isomers.

TABLE I

| Test Material | Aluminum | Time | Remarks |
|---|---|---|---|
| pure VBC | sheet | — | no apparent reaction[1] |
| crude, wet VBC[2] | foil | — | no apparent reaction slow polymerization |
| benzyl chloride[3] | foil | — | vigorous reaction with Al in approximately 3-6 minutes |
| 1:1 styrene-benzyl chloride | foil | — | vigorous reaction |

TABLE I-continued

| Test Material | Aluminum | Time | Remarks |
|---|---|---|---|
| 1:1 vinyltoluene-benzyl chloride | foil | — | vigorous reaction |
| 1:1 VBC-benzyl chloride | foil | 3 days | no apparent reaction |
| pure VBC,[4] | foil | 3 days | no apparent reaction |
| then benzyl chloride | | 30 minutes | usual rapid reaction (see 3 above) delayed 30 min. |
| ethylbenzyl chloride | foil | minutes | rapid reaction with discoloration and gas evolution |
| (α-chlorovinyl)toluene | foil | 3 days | pitting of aluminum and darkening of liquid |
| 1-(chloromethyl)naphthalene | foil | — | vigorous reaction |

[1] There was no visual evidence of reaction or corrosion of the metal, even after the metal surface was scored under the liquid. The liquid itself was crystal clear and colorless.
[2] Crude product from vapor phase chlorination of vinyltoluene at 500° C. after lights were flashed off, contained about ten percent vinylbenzal chloride and vinylbenzotrichloride plus 0.5% each tert-butylpyrocatechol, o-nitrophenol, and dinitro-o-cresol as polymerization inhibitors.
[3] Same results with both pure benzyl chloride and benzyl chloride containing inhibitors as in (2).
[4] The vinylbenzyl chloride was heated at 125° C. for 3 days with no apparent effect on the Al foil, then the benzyl chloride was added and heating was continued.

EXAMPLE 2

Additional liquid phase corrosion tests were run according to the procedure of Example 1 using 0.5-1 g. coupons of various sheet aluminum alloys and of zinc. The vinylbenzyl chloride used was crude product from the vapor phase chlorination of vinyltoluene at about 500° C. from which the low boilers had been flash distilled. It contained about ten percent of higher chlorinated products, largely vinylbenzal chloride and vinylbenzotrichloride plus 0.5% each of tert-butylpyrocatechol, o-nitrophenol, and dinitro-o-cresol as polymerization inhibitors. The tests were run at 125° C. as before for 6 days.

TABLE II

| Metal | Original Weight, grams | Final Weight, grams | Appearance Of Metal |
|---|---|---|---|
| Al 3003 | 0.4545 | 0.4545 | Unchanged |
| Al 1100 | 0.8380 | 0.8385 | Unchanged |
| Al 5052 | 0.8015 | 0.8020 | Unchanged |
| Al 2024-T3 | 0.5800 | 0.5810 | Unchanged |
| Al 6061-0 | 1.0200 | 1.0200 | Unchanged |
| Al 6061-T6 | 0.6845 | 0.6850 | Unchanged |
| Zinc | 0.7210 | 0.7695 | pitted, black resinous layer on surface |

EXAMPLE 3

Coupons of the aluminum alloys identified in Example 2 and a piece of wire mesh packing of 5056 aluminum clad with 6253 aluminum were placed in glass containers with both wet and dry vinylbenzyl chloride so that the metal test pieces were partially immersed in the liquid. The vinylbenzyl chloride used was the isomeric mixture of Example 1. The containers were sealed and stored at room temperature for two months. At the end of this time, there was no visible change in any of the metal test pieces.

EXAMPLE 4

Vinylbenzyl chloride vapor tests were run at various temperatures in the presence of air and nitrogen using as the test apparatus a pair of 200 ml. distillation flasks each connected to a column packed with 3003 Al rings which in turn was topped by a reflux condenser. Both condensers were connected to the same vacuum pump and pressure regulating means whereby the pressure in the system and the vapor temperature in each column was regulated. Each flask had a glass capillary through which air, oxygen, or nitrogen was admitted below the liquid surface. The vinylbenzyl chloride used was the inhibited crude reactor product described in Example 2. One hundred milliliter samples were used in each flask for the separate experiments. Results are tabulated below.

TABLE 3

| Column | Gas | Vapor Temp. °C. | Time, hrs. | Results |
|---|---|---|---|---|
| A | $O_2$ | 125 | 43 | some discoloration and polymerization Al unaffected |
| B | $N_2$ | 125 | 43 | less discoloration, more polymerization than A -Al unaffected |
| A | air | 150 | 14 | polymerized, Al unaffected |
| B | $N_2$ | 150 | 14 | polymerized, Al unaffected |
| A | air | 175 | 4 | polymerized, Al unaffected |
| B | $N_2$ | 175 | 4 | polymerized, Al unaffected |

In all six of the above experiments, the aluminum test pieces appeared to be unchanged by visual examination. Weights of the test pieces either remained the same or increased by a very small amount.

EXAMPLE 5

The general procedure of Example 4 was repeated twice at vapor temperature 125° C. and $N_2$ admitted through the capillary bubbler. The column in each case was packed with 5056 aluminum mesh clad with 6253 aluminum and the still flask also contained some of this aluminum. In one experiment, after 3 hrs. at reflux, 3 ml. of conc. HCl was admitted to the flask in three equal portions, then refluxing was continued for 3 hrs. In the second experiment, anhydrous HCl was admitted through the capillary bubbler for one hour, total reflux time being the same as before.

The concentrated HCl caused some attack on the aluminum and the liquid turned light amber in color. The anhydrous HCl apparently did not attack the aluminum and the liquid appeared unchanged.

EXAMPLES 6-7

Divinylbenzyl chloride (mixed isomers) and ar-bis(-chloromethyl) vinyltoluene (mixed isomers) are contacted with coupons of aluminum under conditions described in the foregoing examples. In each case, no significant decomposition of the organic liquid or corrosion of the aluminum is observed.

The test described in Example 1 was repeated using the same grade of vinylbenzyl chloride and coupons of lead, tantalum, three kinds of stainless steel, tin, copper, brass, mild steel, zinc, Monel metal, and nickel. In each case, the metal surface was attacked to some extent and there was either or both of polymer formation and discoloration of the vinylbenzyl chloride. With zinc, tin, and steel, the reaction was strongly exothermic and a solid mass of cross-linked Friedel-Crafts type of polymer was formed. Results are listed in Table 4.

TABLE 4

| Metal | Results |
| --- | --- |
| Zinc | violent reaction with discoloration, formation of polymer, and attack on metal surface |
| Copper | dark discoloration, some polymer formation, metal attacked |
| Brass | discoloration, metal attacked |
| Lead | polymer formation, metal darkened |
| Tin | much discoloration, severe corrosion of metal, polymer formed |
| Steel | similar to zinc |
| 316 Stainless steel | polymer formation, some darkening of metal |
| 18-8-2 Stainless steel[1] | similar to 316 |
| 20-Cb-3 Stainless steel[2] | more polymer than 316 |
| Nickel | similar to 20-Cb-3 |
| Monel | similar to 20-Cb-3 |
| Tantalum | similar to 20-Cb-3 |

[1] 18% Cr, 18% Ni, 2% Sn
[2] a columbium-containing stainless steel produced by Carpenter Steel Co.

We claim:

1. A method for storing and shipping a compound having the formula

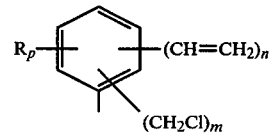

wherein R is an alkyl radical of 1-4 carbon atoms, m and n are independently one or two, and p is zero or one, which method consists of containing said compound in a container of aluminum or alloy having an aluminum content of at least about 90 percent by weight.

2. The method of claim 1 wherein the compound is vinylbenzyl chloride.

3. A method for processing a compound having the formula

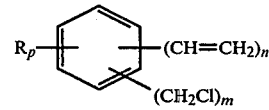

wherein R is an alkyl radical of 1-4 carbon atoms, m and n are independently one or two, and p is zero or one, by distilling, filtering or polymerizing said compound which consists of carrying out said processing in equipment of aluminum or alloy having an aluminum content of at least about 90 percent by weight.

4. The method of claim 3 wherein the processing comprises purification by distillation and the compound is vinylbenzyl chloride.

* * * * *